United States Patent
Baer

(10) Patent No.: US 7,473,401 B1
(45) Date of Patent: Jan. 6, 2009

(54) FLUIDIC EXTRACTION OF MICRODISSECTED SAMPLES

(75) Inventor: Thomas M. Baer, Mountain View, CA (US)

(73) Assignee: MDS Analytical Technologies (US) Inc., Sunnyvale, CA (US)

( * ) Notice: Subject to any disclaimer, the term of this patent is extended or adjusted under 35 U.S.C. 154(b) by 0 days.

(21) Appl. No.: 09/357,423

(22) Filed: Jul. 20, 1999

Related U.S. Application Data

(63) Continuation-in-part of application No. 08/984,983, filed on Dec. 4, 1997, now Pat. No. 5,985,085.

(60) Provisional application No. 60/093,744, filed on Jul. 21, 1998.

(51) Int. Cl.
*B01L 3/00* (2006.01)

(52) U.S. Cl. .................... 422/102; 422/101

(58) Field of Classification Search .......... 422/101, 422/108, 129, 103, 50, 63, 102, 104; 436/518, 436/524, 528, 180; 435/4, 6
See application file for complete search history.

(56) References Cited

U.S. PATENT DOCUMENTS

| | | | |
|---|---|---|---|
| 1,093,211 A | 4/1914 | Schulhoff | 220/789 |
| 2,801,568 A | 8/1957 | Dakin | 88/40 |
| 3,680,947 A | 8/1972 | Wanesky | 350/81 |
| 3,705,769 A | 12/1972 | Johannsmeier | 355/91 |
| 3,848,962 A | 11/1974 | Nelson | 350/86 |
| 3,940,250 A * | 2/1976 | Plakas et al. | 435/8 |
| 4,149,803 A | 4/1979 | Litz | 356/244 |
| 4,210,384 A | 7/1980 | Meyer et al. | 350/19 |
| 4,303,866 A | 12/1981 | Porro et al. | 350/442 |
| 4,436,385 A | 3/1984 | Fischer et al. | 350/529 |
| 4,508,435 A | 4/1985 | Graham et al. | 350/529 |
| 4,509,834 A | 4/1985 | Hodgson | 350/521 |
| 4,538,885 A | 9/1985 | Graham et al. | 350/529 |

(Continued)

FOREIGN PATENT DOCUMENTS

CH 566 015 8/1975

(Continued)

OTHER PUBLICATIONS

Ashkin, A. and Dziedzic, J.M. "Internal cell manipulation using infrared laser traps," *Proc. Nat. Acad. Sci. USA*, 86:7914-7918 (1989).

(Continued)

*Primary Examiner*—Jill Warden
*Assistant Examiner*—Natalia Levkovich
(74) *Attorney, Agent, or Firm*—Fish & Richardson P.C.

(57) ABSTRACT

Systems and methods are described for processing of laser capture microdissection (LCM) samples. A biological sample processing system includes a laminated film sample processing device including a reaction chamber mated with a biological sample carrier to form a fluidic circuit. A multiple step fluidic device includes an LCM transfer film and a surface that is spaced apart from the transfer film so as to define a fluid volume. The reaction buffer can be removed through an exit port, or stop junction, in the surface. Advantages of the systems and methods include facilitating subsequent processing reducing the volume of reagents and enhancing economy. For instance, the reaction buffer can be conveniently removed away from the LCM transfer film.

33 Claims, 15 Drawing Sheets

Full Assembly

U.S. PATENT DOCUMENTS

| | | | |
|---|---|---|---|
| 4,552,033 A | 11/1985 | Marzhauser | 74/479 |
| 4,600,282 A | 7/1986 | Yamamura et al. | 353/122 |
| 4,614,431 A | 9/1986 | Komeyama | 356/401 |
| 4,627,009 A | 12/1986 | Holmes et al. | 364/559 |
| 4,673,267 A | 6/1987 | Erxleben | 350/531 |
| 4,702,565 A | 10/1987 | Schilling et al. | 350/531 |
| 4,731,530 A | 3/1988 | Mikan | 350/229 |
| 4,807,984 A | 2/1989 | Kurimura et al. | 350/529 |
| 4,824,229 A | 4/1989 | Narita et al. | 350/531 |
| 4,836,667 A | 6/1989 | Ozeki | 350/531 |
| 4,852,985 A | 8/1989 | Fujihara et al. | 350/523 |
| 4,856,873 A | 8/1989 | Kleinberg | 350/502 |
| 4,871,245 A | 10/1989 | Ishikawa et al. | 350/502 |
| 4,920,053 A | 4/1990 | Inoue et al. | 435/240.1 |
| 4,923,294 A | 5/1990 | Courtenay | 350/529 |
| 4,964,708 A | 10/1990 | Mason | 350/519 |
| 4,992,660 A | 2/1991 | Kobayashi | 250/306 |
| 5,029,791 A | 7/1991 | Ceccon et al. | 248/287 |
| 5,057,689 A | 10/1991 | Nomura et al. | 250/310 |
| 5,077,620 A | 12/1991 | Mauro | 359/393 |
| 5,089,909 A | 2/1992 | Kleinberg | 359/363 |
| 5,103,338 A | 4/1992 | Crowley et al. | 359/394 |
| 5,126,877 A | 6/1992 | Biber | 359/389 |
| 5,158,895 A | 10/1992 | Ashihara et al. | 436/526 |
| 5,162,941 A | 11/1992 | Favro et al. | 359/386 |
| 5,165,297 A | 11/1992 | Krueger | 74/479 |
| 5,173,802 A | 12/1992 | Heller | 359/384 |
| 5,173,803 A | 12/1992 | Heller | 359/384 |
| 5,192,503 A | 3/1993 | McGrath et al. | 422/57 |
| 5,253,110 A | 10/1993 | Ichihara et al. | 359/619 |
| 5,262,891 A | 11/1993 | Nakasato | 359/385 |
| 5,263,384 A | 11/1993 | Suzuki | 74/479 MF |
| 5,280,384 A | 1/1994 | Shibasaki | 359/396 |
| 5,288,996 A | 2/1994 | Betzig et al. | 250/227.26 |
| 5,296,963 A | 3/1994 | Murakami et al. | 359/389 |
| 5,312,393 A | 5/1994 | Mastel | 606/4 |
| 5,323,009 A | 6/1994 | Harris | 250/458.1 |
| 5,337,178 A | 8/1994 | Kung et al. | 359/393 |
| 5,345,333 A | 9/1994 | Greenberg | 359/389 |
| 5,357,366 A | 10/1994 | Marchlenski | 359/393 |
| 5,359,417 A | 10/1994 | Muller et al. | 356/375 |
| 5,367,401 A | 11/1994 | Saulietis | 359/398 |
| 5,386,112 A | 1/1995 | Dixon | 250/234 |
| 5,393,647 A | 2/1995 | Neukermans et al. | 430/320 |
| 5,403,970 A | 4/1995 | Aoki | 84/626 |
| 5,412,503 A | 5/1995 | Nederlof | 359/393 |
| 5,415,994 A * | 5/1995 | Imrich et al. | 435/5 |
| 5,420,716 A | 5/1995 | Fukaya | 359/368 |
| 5,434,703 A | 7/1995 | Morizumi | 359/385 |
| 5,439,650 A * | 8/1995 | Tsugita et al. | 422/108 |
| 5,450,233 A | 9/1995 | Yamamoto et al. | 359/368 |
| 5,451,500 A * | 9/1995 | Stapleton | 435/6 |
| 5,455,420 A | 10/1995 | Ho et al. | 250/306 |
| 5,468,967 A | 11/1995 | Chan et al. | 250/397 |
| 5,471,260 A | 11/1995 | Luce et al. | 351/263 |
| 5,479,252 A | 12/1995 | Worster et al. | 356/237 |
| 5,486,335 A | 1/1996 | Wilding et al. | 422/55 |
| 5,494,646 A | 2/1996 | Seymour | 422/101 |
| 5,504,366 A | 4/1996 | Weiss et al. | 73/863 |
| 5,506,725 A | 4/1996 | Koike et al. | 359/388 |
| 5,510,615 A | 4/1996 | Ho et al. | 250/306 |
| 5,513,768 A | 5/1996 | Smith | 220/259 |
| 5,517,353 A | 5/1996 | Ikoh et al. | 359/388 |
| 5,532,476 A | 7/1996 | Mikan | 250/221 |
| 5,532,873 A | 7/1996 | Dixon | 359/388 |
| 5,535,052 A | 7/1996 | Jorgens | 359/388 |
| 5,536,941 A | 7/1996 | Swann | 250/311 |
| 5,537,863 A | 7/1996 | Fujiu et al. | 73/105 |
| 5,552,928 A | 9/1996 | Furuhashi et al. | 359/379 |
| 5,557,456 A | 9/1996 | Garner et al. | 359/393 |
| 5,558,329 A | 9/1996 | Liu | 273/148 B |
| 5,559,329 A | 9/1996 | Joseph et al. | 250/306 |
| 5,587,748 A | 12/1996 | Luce et al. | 351/208 |
| 5,587,833 A | 12/1996 | Kamentsky | 359/393 |
| 5,598,888 A | 2/1997 | Sullivan et al. | 165/263 |
| 5,602,674 A | 2/1997 | Weissman et al. | 359/393 |
| 5,619,035 A | 4/1997 | Weiss et al. | 250/306 |
| 5,621,207 A | 4/1997 | O'Mara | 250/221 |
| 5,624,554 A * | 4/1997 | Faulkner et al. | 210/232 |
| 5,627,041 A * | 5/1997 | Shartle | 435/7.24 |
| 5,638,206 A | 6/1997 | Sumiya et al. | 359/368 |
| 5,639,428 A | 6/1997 | Cottingham | 422/112 |
| 5,641,896 A | 6/1997 | Karrai | 73/105 |
| 5,659,421 A | 8/1997 | Rahmel et al. | 359/391 |
| 5,741,710 A * | 4/1998 | Ek | 436/73 |
| 5,763,191 A | 6/1998 | Knoll et al. | 435/7.1 |
| 5,843,657 A | 12/1998 | Liotta et al. | 435/6 |
| 5,859,699 A | 1/1999 | Baer et al. | 356/246 |
| 5,860,937 A | 1/1999 | Cohen | 600/576 |
| 5,912,134 A | 6/1999 | Shartle | 435/7.24 |
| 5,936,858 A * | 8/1999 | Arai | 436/45 |
| 6,043,080 A * | 3/2000 | Lipshutz et al. | 435/287.2 |
| 6,057,165 A * | 5/2000 | Mansour | 436/518 |
| 6,084,237 A * | 7/2000 | Troster et al. | 250/288 |
| 6,084,660 A * | 7/2000 | Shartle | 356/39 |
| 6,221,655 B1* | 4/2001 | Fung et al. | 435/288.1 |
| 6,277,648 B1* | 8/2001 | Colpan | 436/177 |
| 6,720,191 B1* | 4/2004 | Goldstein et al. | 436/174 |

FOREIGN PATENT DOCUMENTS

| | | |
|---|---|---|
| DE | 196 03 996 A1 | 8/1997 |
| EP | 0 388 168 | 9/1990 |
| WO | WO 91/07683 | 5/1991 |
| WO | WO 95/23960 | 9/1995 |
| WO | WO 95/30919 | 11/1995 |
| WO | WO 97/13838 | 4/1997 |
| WO | WO 98/35215 | 8/1998 |
| WO | WO 98/35216 | 8/1998 |

OTHER PUBLICATIONS

Bonner, R. F. et al. "Laser capture microdissection: Molecular analysis of tissue," *Science*, 278:1481-1483 (1997).

Emmert-Buck, M.R. et al. "Laser Capture Microdissection," *Science*, 274:998-1001 (1996).

Friend, T. "Getting up close to cancer genes," printed in *USA Today*, Science section, p. 4D, Aug. 5, 1977.

Fukui, K. et al. "Microdissection of plant chromosomes by argon-ion laser beam," *Theoretical & Applied Genetics*, 84:787-791 (1992).

Geduspan, J. et al., "A Growth-Promoting Influence from the Mesonephros during Limb Outgrowth" *Developmental Biology*, 151(1):242-250 (1992).

Isenberg, G. et al., "Cell surgery by laser micro-dissection: a preparative method". *Journal of Microscopy*, vol. 107, Pt. 1, pp. 19-24 (1976).

Jiménez, C. R. et al. "Neuropeptide expression and processing as revealed by direct matrix-assisted laser desorption ionization mass spectrometry of single neurons," *Journal of Neurochemistry*, 62(1):404-407 (1994).

Kubo, Y.i et al. "Early detection of Knudson's two-hits in preneoplatics renal cells of the Eker rat model by the laser microdissection procedure," *Cancer Research*, 55(5):989-990 (1995).

Meier-Ruge, W. et al. "The laser in the Lowry technique for microdissection of freeze-dried tissue slices," *Histochemical Journal*, 8:387-401 (1976).

Schindler, M. et al. "Automated analysis & survival selection of anchorage-dependent cells under normal growth conditions," *Cytometry*, 6(4):368-374 (1985).

Schindler, Melvin et al. "Select, microdissect & eject," *Nature Biotechnology*, 16(8):719-720 (1998).

Schültze, K. and Lahr, G. "Identification of expressed genes by laser-mediated manipulation of single cells," *Nature Biotechnology*, 16:737-742 (1998).

Veigel, C. et al. "New cell biological applications of the laser microbeam technique: the microdissection and skinning of muscle fibers and the perforation and fusion of sarcolemma vesicles," *European Journal of Cell Biology*, 63(1):140-148 (1994).

* cited by examiner

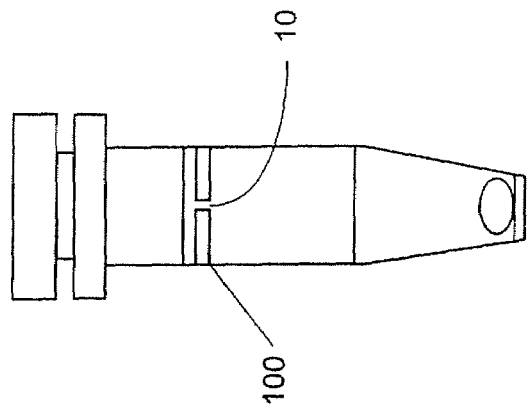
Figure 4  Figure 5  Figure 6
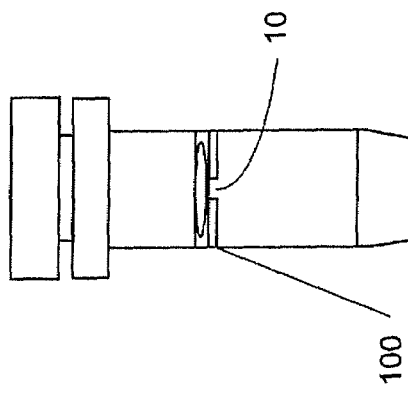
Figure 7
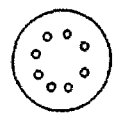
Figure 8
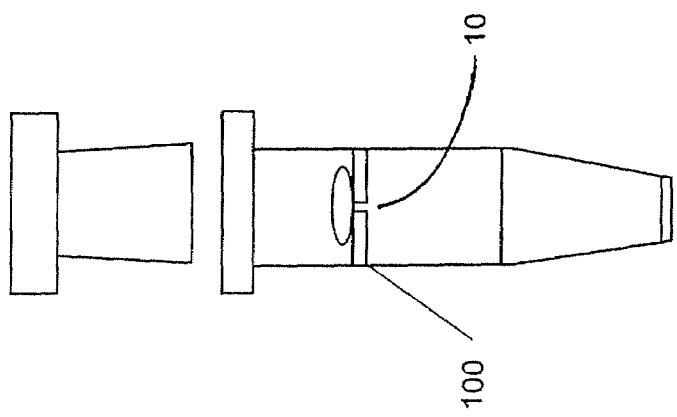

Adhesive (Layer 2)

Bottom (Layer 1)

Ring (Layer 4)

Full Assembly

Top (Layer 3)

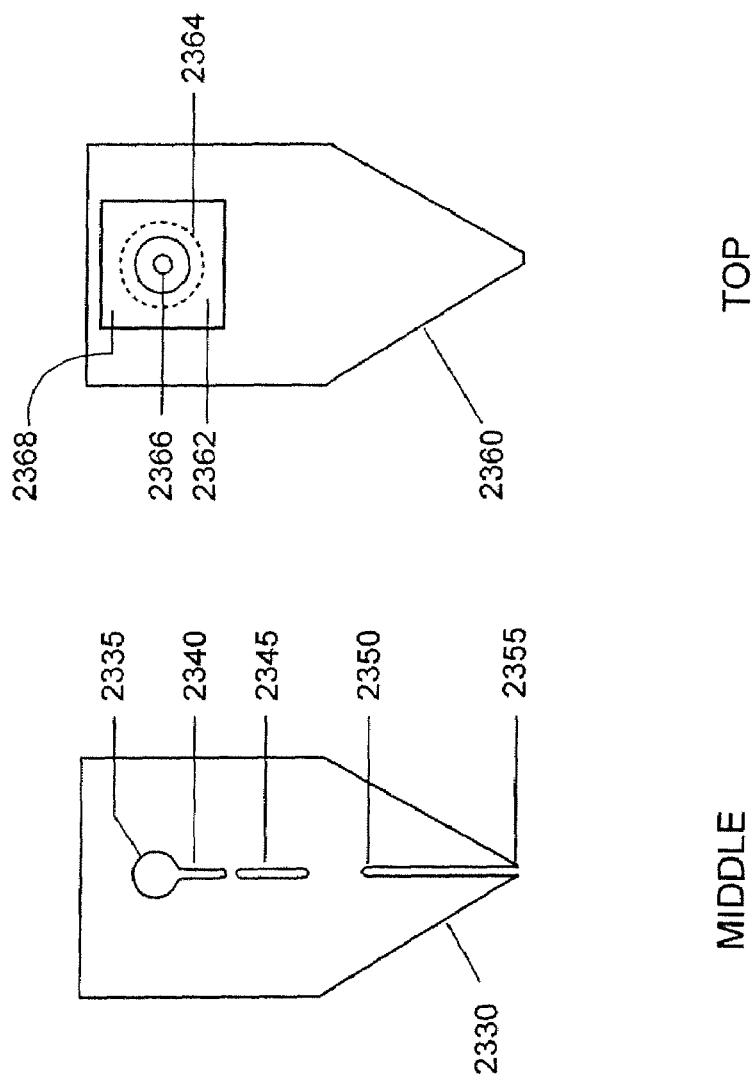

RING 1

RING 2

RING 2 COVER

FLUIDIC EXTRACTION OF MICRODISSECTED SAMPLES

CROSS-REFERENCE TO RELATED APPLICATION

This application is a continuation-in-part under 35 U.S.C. § 120 of copending U.S. Ser. No. 60/093,744, filed Jul. 21, 1998; and 08/984,983, filed Dec. 4, 1997, now issued as U.S. Pat. No. 5,985,085, the entire contents of both of which are hereby incorporated herein by reference as if fully set forth herein.

BACKGROUND OF THE INVENTION

1. Field of the Invention

The invention relates generally to the liquid extraction of microdissected samples. More particularly, the invention relates to the liquid extraction of microdissected tissue samples through fluidic circuits, including the interrelationships between microdissection sample carriers and microdissection analysis vessels.

2. Discussion of the Related Art

Prior art microdissection techniques and processing are known to those skilled in the art. For example, a conventional microdissection is typically is typically performed with small surgical instruments.

A problem with this technology has been that subsequent processing of the microdissected sample is difficult because of the small size of the sample. Therefore, what is required is solution that facilitates processing of microdissected samples.

Another problem with this technology has been that use of a relatively large amount of reaction buffer and/or subsequent reagents, which dilutes the sample constituents, can make obtaining data from the comparatively small sample difficult. Therefore, what is also required is a solution that uses a smaller volume of reaction buffer and/or other reagents.

One approach, in an attempt to solve the above-discussed problems involves using a carrier film to capture and transport the microdissected sample. This film and sample are then both dropped into the centrifuge tube where the sample is contacted by the reaction buffer. However, this approach does not necessarily reduce the volume of reaction buffer and/or subsequent reagents.

In addition, the previous approaches generally require sequential handling of samples, reaction buffer and subsequent reagents in separate apparatus, which involves many manual handling steps leading to possible human error and relatively high cost. Therefore, what is also needed is a solution that meets the above-discussed requirements in a more cost effective manner.

Heretofore, the requirements of facilitating subsequent processing, reducing the volume of reagents, and economy referred to above have not been fully met. What is needed is a solution that simultaneously addresses all of these requirements. The invention is directed to meeting these requirements, among others.

SUMMARY OF THE INVENTION

A goal of the invention is to simultaneously satisfy the above-discussed requirements of facilitating and simplifying subsequent processing, reducing the volume of reagents, and economy which, in the case of the prior art, are mutually contradicting and are not simultaneously satisfied.

One embodiment of the invention is based on a biological sample processing system, comprising: a laminated film sample processing device including a reaction chamber mated with a biological sample carrier to form a fluidic circuit. Another embodiment of the invention is based on a fluidic circuit, comprising: a reaction chamber; a sample carrier mating surface coupled to said reaction chamber; and a conduit coupled to said reaction chamber. Another embodiment of the invention is based on a method of processing a biological sample, comprising: providing a sample carrier with a biological sample; and mating said sample carrier to a laminated film sample processing device having a reaction chamber to form a fluidic circuit, wherein said biological sample is positioned within said reaction chamber. Another embodiment of the invention is based on a microdissected sample extraction device, comprising: a fill port defined at least in part by a middle laminate layer and a bottom laminate layer; a fill port-to-reaction chamber capillary coupled to said fill port, said fill port-to-reaction chamber capillary defined at least in part by said middle laminate layer, said bottom laminate layer and a top laminate layer, said fill port-to-reaction chamber capillary defining a middle stop junction that extends through said top laminate layer; a spacer coupled to said top laminate layer, said spacer including a microdissected sample film carrier mating surface; an reaction chamber coupled to said fill port-to-reaction chamber capillary through said middle stop junction, said reaction chamber defined at least in part by said top laminate layer and said spacer; and an reaction chamber exit capillary coupled to said reaction chamber, said reaction chamber exit capillary defined at least in part by said middle laminate layer, said bottom laminate layer and said top laminate layer, said extraction chamber exit capillary defining a second stop junction that extends through said top laminate layer and couples with said reaction chamber. Another embodiment of the invention is based on an apparatus, comprising: a multiple step fluidic device for laser capture microdissection, said multiple step fluidic device including a transfer film containing the sample to be analyzed and a surface that is spaced apart from said transfer film so as to define a fluid volume, said surface being connected to an exit stop junction that functions as an exit port for a reaction buffer. Another embodiment of the invention is based on a method, comprising: providing a multiple step fluidic device for laser capture microdissection, said multiple step fluidic device including i) a transfer film to which a portion of a sample is adhered and ii) a surface that is spaced apart from said transfer film so as to define a fluid volume, said surface being connected to an exit stop junction that functions as an exit port for a reaction buffer; contacting said portion with said reaction buffer; and then removing said reaction buffer from said fluid volume.

These, and other, goals and embodiments of the invention will be better appreciated and understood when considered in conjunction with the following description and the accompanying drawings. It should be understood, however, that the following description, while indicating preferred embodiments of the invention and numerous specific details thereof, is given by way of illustration and not of limitation. Many changes and modifications may be made within the scope of the invention without departing from the spirit thereof, and the invention includes all such modifications.

BRIEF DESCRIPTION OF THE DRAWINGS

A clear conception of the advantages and features constituting the invention, and of the components and operation of model systems provided with the invention, will become more readily apparent by referring to the exemplary, and therefore nonlimiting, embodiments illustrated in the drawings accompanying and forming a part of this specification, wherein like reference characters (if they occur in more than one view) designate the same parts. It should be noted that the features illustrated in the drawings are not necessarily drawn to scale.

FIG. 4 illustrates a side schematic view of a microcentrifuge tube and cap, representing an embodiment of the invention incorporating a smaller transfer film area.

FIG. 5 illustrates a side schematic view of the microcentrifuge tube and cap of FIG. 4 with the cap inserted into the tube, representing an embodiment of the invention.

FIG. 6 illustrates a side schematic view of the microcentrifuge tube and cap of FIGS. 4 and 5 after spinning, representing an embodiment of the invention.

FIG. 7 illustrates a top schematic view of an insert or plug incorporating a stop junction, representing an embodiment of the invention.

FIG. 8 illustrates a side schematic view of another insert or plug, representing an embodiment of the invention.

DESCRIPTION OF PREFERRED EMBODIMENTS

Figure 1:
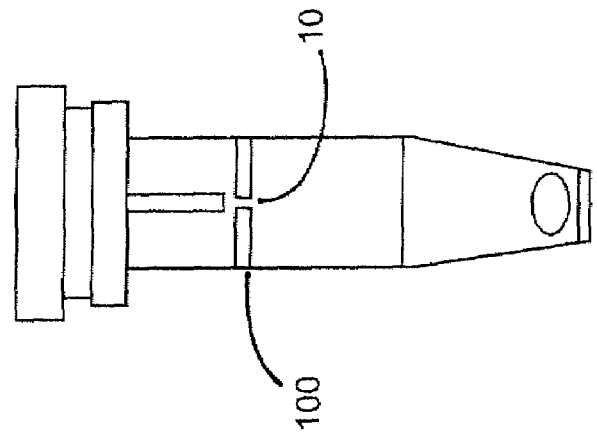
FIG. 1 illustrates a side schematic view of a microcentrifuge tube and cap, representing an embodiment of the invention.

The invention and the various features and advantageous details thereof are explained more fully with reference to the nonlimiting embodiments that are illustrated in the accompanying drawings and detailed in the following description. Descriptions of well known components and processing techniques are omitted so as not to unnecessarily obscure the invention in detail.

The invention includes any laminated film device mated with any microdissected sample carrier to form a fluidic circuit. The laminated film device can be termed an extraction device. The microdissected samples can be obtained in any manner including, for example, laser capture microdissection, laser pressure catapulting, laser trapping, laser cutting and/or ablation, mechanical cutting, etceteras.

The invention can include an extraction chamber. The extraction chamber can be defined in part by the sample carrier. The extraction chamber can also be defined in part by a spacer ring. By first aligning the microdissected sample that is being carried by the sample carrier within the interior of the spacer ring, and then mating the sample carrier with the spacer ring, the microdissected sample on the surface of the carrier can be cleanly introduced into the extraction chamber. Before use, the extraction chamber can be kept clean by providing a release layer on the mating surface of the spacer ring.

The invention can include one or more capillaries. The capillaries are pipes or conduits that permit mass transport within the extraction device. An end of a capillary where fluid flows and then stops can be termed a stop junction. A capillary end where fluid is introduced can be termed a fluid well or fluid port. The capillaries can couple structure features located within, or outside, the extraction device. The stop junction(s) and/or fill port(s) can be upgraded with the addition of pump. Such a pump can be a simple externally actuated bubble (aka blister) formed in one, or more, of the laminate layers. An intervening resilient layer (e.g., foam) can make the operation of such a bubble pump more effective, reliable and predictable. The pump blister can have a hole that can be covered by the operator's finger so that when covered and the pump blister is depressed the increase in air pressure in the fluidic circuit causes fluid to move in the circuit. The pump blister hole can also act as a fluid well or fluid port.

Mass (i.e., fluid, solid and gas) can be driven through the capillaries by capillary force(s), pumping force(s) and/or acceleration force(s) (e.g., centripetal acceleration from a laboratory centrifuge into which the entire extraction device can be placed). To fill and/or empty a chamber, a pump or acceleration force is usually required. Extraction devices that are shaped to fit at least partially into centrifuge tubes can be termed darts, which is descriptive of their shape.

The flow rate of fluid within the capillary can be controlled by the diameter of the capillary. The volumetric flow rate within the capillaries can be a function of the hydrostatic pressure. Thus, a large volume of fluid at a well generating a large head pressure will tend to result in a higher flow rate. The ratio of a capillary inlet diameter to a capillary outlet diameter can be used to control the volumetric flow. For instance, a small capillary pulling from large well will have a higher volumetric flow than the same capillary pulling from smaller well. Capillary forces can also be used to move the fluid through the device. By manufacturing the device out of hydrophilic materials the water based fluid will be drawn into the capillaries by capillary action. The fluid will move until it reaches an exit port with a small diameter, i.e. a stop junction. The fluid can be forced through the stop junction by increasing the forces on the fluid, for example by using centrifugal acceleration or increased air pressure. In this manner fluids can be drawn in to a certain portion of the device for digestion or incubation and then at a later time the fluids can be moved into a different portion of the device by applying said forces for subsequent dilution or analysis.

The invention can include a dilution chamber defined by the laminated film device. A dilutent can be added to the device after the digestion reagents and the device can be placed in a centrifuge to move the dilutent plus the digested sample into a dilution chamber. The invention can also include reagents deposited in the chamber(s), conduit(s), well(s) and/or stop junction(s) to change the surface tension or hydrophilicity of the laminate material, or even the fluid. The deposited reagents can also include digestion compounds, analysis reagents such as antibodies or nucleic acid probes.

The context of the invention is microdissected sample analysis, especially cellular tissue analysis. In addition to being mated to the sample film carrier, the extraction device can be coupled to other analysis equipment such as a filter, a hybridization chamber, a PCR chamber, assay equipment, etceteras.

The particular manufacturing process used for fabricating the laminated extraction devices should be inexpensive and reproducible. The laminate layers can be processed by standard laminated film converting process incorporating mechanical punching or cutting of continuous rules of laminated films and assembly onto reels. This process is well known to those skilled in the art and is called a web based process. The devices can also be manufactured by a combination of mechanical and laser cutting (e.g., 25 W CO2 laser). The laminate layers can be joined by a continuous roll calendering or adhesive process. The laminate layers can also be joined (or additional structural components, such as covers, added) by ultrasonic welding and/or heat staking.

However, the particular manufacturing process used for fabricating the laminated extraction devices is not essential to the invention as long as it provides the described functionality. Normally those who make or use the invention will select the manufacturing process based upon tooling and energy requirements, the expected application requirements of the final product, and the demands of the overall manufacturing process.

The particular material used for laminated extraction devices should be biologically and chemically inert. It is preferred that the laminate materials be a hydrophilic polymer. For the manufacturing operation, it is an advantage to employ a polyester material. Selected areas of the materials can have surface treatment to direct and control the flow of fluid such as texturing and/or plasma or chemical treatment. These treatments can vary the surface tension to make the materials more wettable.

However, the particular material selected for laminated extraction devices is not essential to the invention, as long as it provides the described function. Normally, those who make or use the invention will select the best commercially available material based upon the economics of cost and availability, the expected application requirements of the final product, and the demands of the overall manufacturing process.

A purpose of the invention is to provide a method for extracting cellular material from a laser capture microdissection (LCM) film that might employ a variety of different geometries, and require a small volume of reaction buffer. Current techniques require inserting the LCM film carrier into the fluid. After the extraction reaction the LCM film carrier is removed from the reaction buffer and the liquid reaction buffer is then processed in subsequent stages. It is desirable to have a simple, convenient method to remove the reaction buffer from the film carrier prior to extracting the film carrier so that the liquid is not lifted from the reaction vessel when the film carrier is removed from the buffer.

One method to achieve this goal is to incorporate a simple stop junction into the design of a microcentrifuge tube as illustrated in FIGS. 1-8. This stop junction can consist of a small hole 10 or multiple holes in an insert in the tube that prevents the fluid from passing through the hole unless some force, say a centrifugal force, is applied to the liquid. The force required to cause the fluid to pass through the hold can be adjusted by varying the size of the hole.

Figure 2:
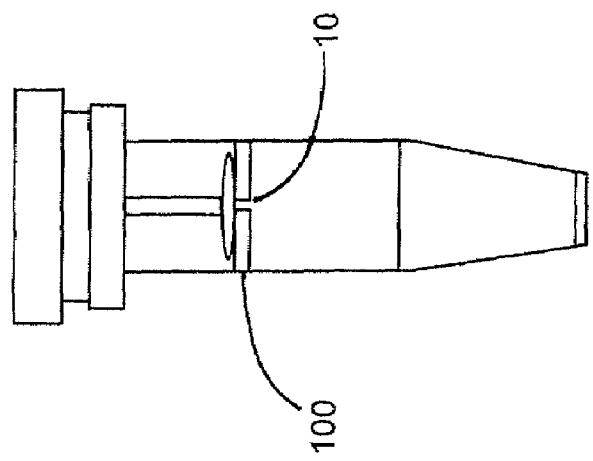
FIG. 2 illustrates a side schematic view of the microcentrifuge tube and cap of FIG. 1 with the cap inserted into the tube, representing an embodiment of the invention.
Figure 3:
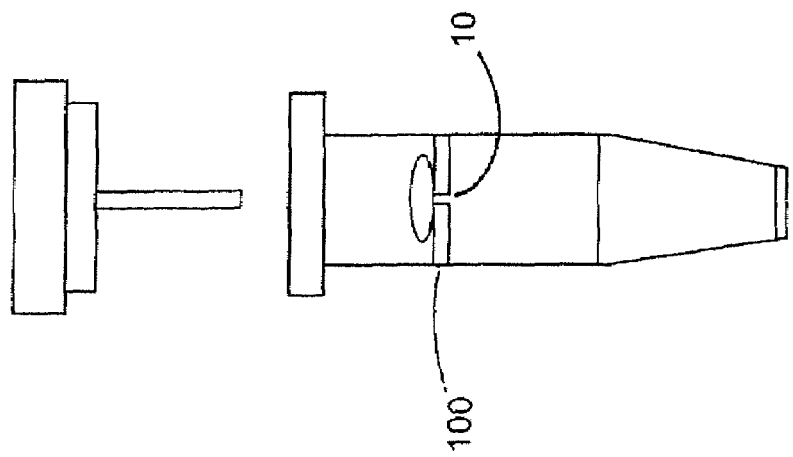
FIG. 3 illustrates a side schematic view of the microcentrifuge tube and cap of FIGS. 1 and 2 after spinning, representing an embodiment of the invention.

Referring to FIGS. 1-8, the processing steps include (a) applying the buffer to the top of the insert 100, as shown in FIGS. 1 and 4. The buffer is prevented from penetrating the insert 100 by the stop junction forces. Then (b) the fluid, and therefore the size of the vessel, is adjusted so as to prevent forcing the fluid completely through the hole when the film carrier inserted into the tube, as shown in FIGS. 2 and 5. Extraction takes place with the apparatus in the configuration illustrated in FIGS. 2 and 5. After extraction, the reaction vessel assembly is placed in a centrifuge (c) and spun at a velocity to supply sufficient force to move the liquid past the stop junction and into the reservoir, as shown in FIGS. 3 and 6. The film carrier is then removed without disturbing the fluid contents. The fluid can be removed from the reagent vessel using a thin pipette or a syringe. Inserts or plugs, as shown in FIGS. 7-8, can be utilized inside the vessel.

Alternative Embodiments

A purpose of the invention is to provide a LCM film carrier that has a large surface area in order to cover a large portion of the tissue sample and yet require a small liquid volume to digest the transferred tissue. This can be accomplished by providing a laser capture microdissection (LCM) film carrier as part of a capillary assembly.

Figure 10:
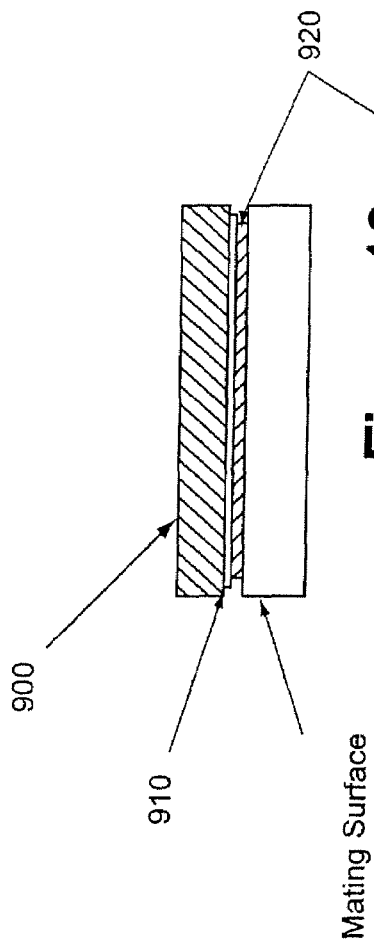
FIG. 10 illustrates a side schematic view of a laminated film device mated with the film of a laser capture microdissection film carrier to form a fluidic circuit, representing an embodiment of the invention.
Figure 11:
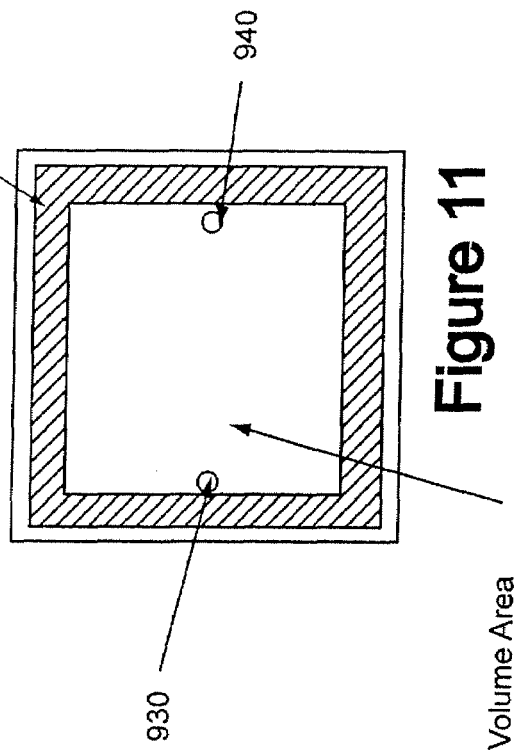
FIG. 11 illustrates a top schematic view of the fluidic circuit shown in FIG. 10, representing an embodiment of the invention.
Figure 9:
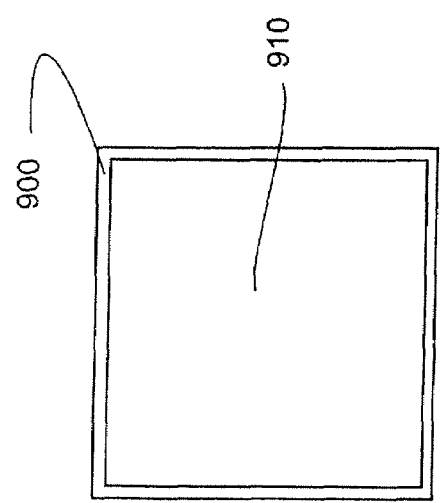
FIG. 9 illustrates a top schematic view of a laser capture microdissection film carrier, representing an embodiment of the invention.

The invention incorporates an LCM film carrier 900, as shown in FIG. 9, into a fluidic assembly that allows a thin layer of the liquid to contact the film. The film 910 can be spaced off from a mating surface by a precision spacer that can include of a piece of double sided adhesive 920 of an appropriate thickness, for example, approximately 100 microns. This tape creates a gap between the film carrier and the mating surface as indicated in FIG. 10 and seals the liquid in to the interior area of the film carrier. An appropriate volume of liquid reagents are applied to the mating surface prior to sealing with the film carrier. Referring to FIG. 11, the liquid is extracted from the sealed assembly through an exit port 930 by applying air pressure to the vent hole 940. Or alternatively, the assembly can be inserted in a centrifuge and with the exit port at a larger radius then the vent hole and the exit port attached to a suitable reagent vessel. This assembly can be rotated at sufficient angular velocity to overcome the stop junction forces and empty the fluid through the exit port and into the reagent vessel.

Figure 13:
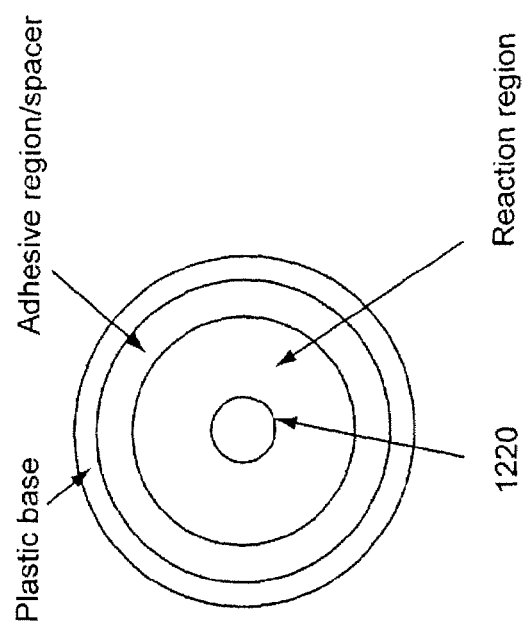
FIG. 13 illustrates a side schematic view of a laminated extraction capillary/stop junction assembly, representing an embodiment of the invention.
Figure 12:
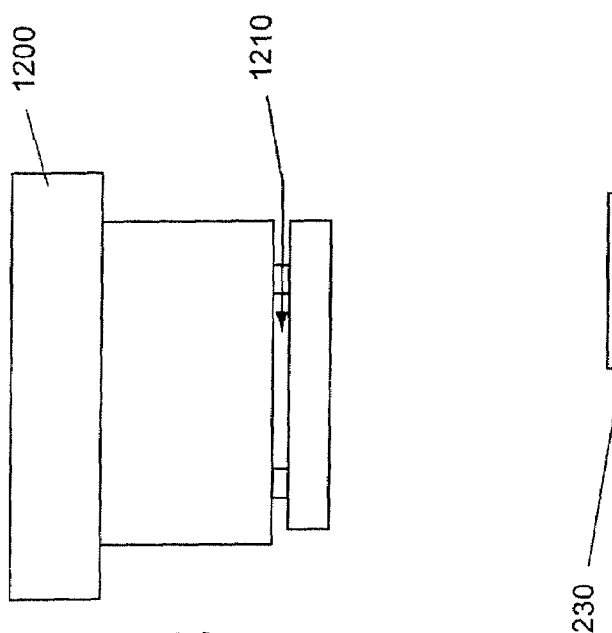
FIG. 12 illustrates a side schematic view of a cap sealed to a laminated assembly, representing an embodiment of the invention.
Figure 14:
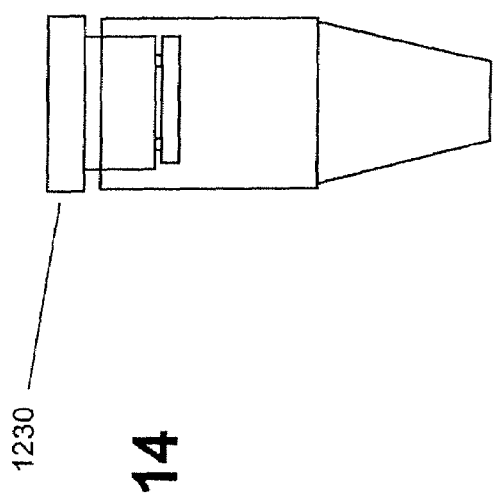
FIG. 14 illustrates a side schematic view of the cap/laminate of FIG. 12 inserted into a microcentrifuge tube, representing an embodiment of the invention.

Turning to FIGS. 12-14, the alternative embodiment is shown embodied in combination with a microcentrifuge tube assembly. In FIG. 12, the cap 1200 that carries the LCM transfer film is spaced away from the mating surface with a double sided adhesive spacer so as to define a fluid volume 1210. In FIG. 13 the exit stop junction 1220 of the mating surface can be seen. Multiple vent holes can be used to allow application port and air vents so that the reagents can be applied through the application port after assembly of the device. Liquid can be loaded onto the center of the laminate assembly and then the cap can be placed on top. The liquid volume can be metered so as to fill the reaction region and wet the surface of the cap (i.e., the LCM transfer film and acquired portion of sample) but not be forced out through stop junction. Cap/laminate assembly 1230 is then inserted into a microcentrifuge tube. After reaction, the microcentrifuge tube assembly can be spun at a sufficient rotational velocity to allow fluid to pass through stop junction and rest in the bottom of tube. This technique will also work with microtiter plates.

EXAMPLES

Specific embodiments of the invention will now be further described by the following, nonlimiting examples which will serve to illustrate in some detail various features of significance. The examples are intended merely to facilitate an understanding of ways in which the invention may be practiced and to further enable those of skill in the art to practice the invention. Accordingly, the examples should not be construed as limiting the scope of the invention.

Example 1

For a typical geometry it can be assumed that the film carrier has dimensions of 1 cm. by 1 cm. and that the double sided tape thickness is 100 microns. The resulting enclosed volume will be only 10 mm$^3$ or 10 microliters. At a rotational velocity of 1,000 rpm-30,000 the forces exerted on the enclosed liquid can be sufficient to cause the extraction product to pass through a stop junction that is contiguous with the enclosed volume and be collected in the bottom of a tube.

Example 2

Figure 15:
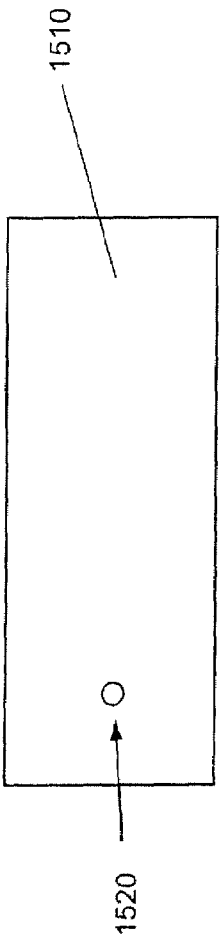
FIG. 15A illustrates a top schematic view of the bottom laminate of an extraction device, representing an embodiment of the invention.
FIG. 15B illustrates a top schematic view of the middle laminate of an extraction device, representing an embodiment of the invention.
FIG. 15C illustrates a top schematic view of the top laminate of an extraction device, representing an embodiment of the invention.
FIG. 15D illustrates a side schematic view of the laminates depicted in FIGS. 15A-15C together with a microdissected sample carrier, representing an embodiment of the invention.
Figure 15:
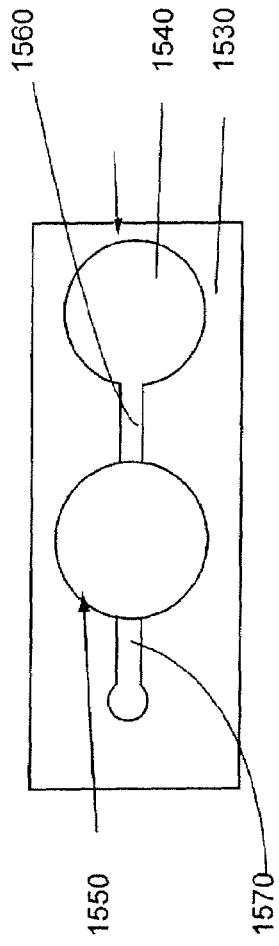
Figure 15:
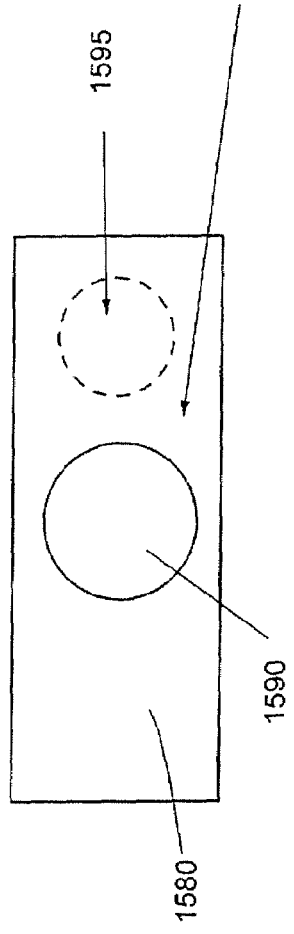
Figure 15:
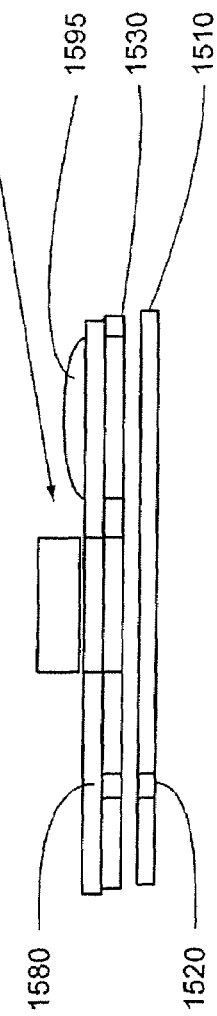

Referring to FIGS. 15A-15D, a single stage extraction device with a pump is depicted. Referring to FIG. 15A, this single stage extraction device includes a base laminate 1510. The base laminate 1510 includes an exit port 1520.

Referring to FIG. 15B, this single stage extraction device includes a middle laminate 1530. The middle laminate 1530 includes a first orifice defining a pump area 1540. The middle laminate 1530 includes a second orifice defining a reaction area 1550. The reaction area 1550 can correspond to a three-dimensional extraction chamber. The pump area 1540 is connected to the reaction area 1550 via a first capillary 1560. A second capillary 1570 is also connected to the reaction area 1550. The middle laminate 1530 can be made of a sheet of polymer having a first sticky side and a second sticky side, thereby defining a double adhesive layer.

Referring to FIG. 15C, this single stage extraction device includes a top laminate 1580. The top laminate 1580 includes a first orifice 1590 that is coincident with the reaction area 1550. Together, the second orifice of the middle laminate 1530 and the first orifice of the top laminate 1580 cooperate to define a extraction chamber for extraction of components from the sample. The top laminate 1580 includes a bi-position pump blister 1595 that is coincident with the pump area 1540.

Referring to FIG. 15D, the base laminate 1510, the middle laminate 1530, and the top laminate 1580 can be seen joined together to form the single stage extraction device. A film carrier 1505 is depicted adjacent the top laminate 1580. Together, the bottom of the film carrier 1505, the first orifice 1590 and the reaction area 1550 cooperate to define the extraction chamber.

The operation of this single stage extraction device will now be described. The pump area 1540 can be provided with a reaction buffer (aka extraction fluid). A microdissected sample on the film carrier 1505 is then introduced, and the extraction chamber closed, by placing the film carrier 1505 on the top surface of the top laminate 1580. The bi-position pump blister 1595 is then actuated to force reaction buffer into the extraction chamber so that it contacts the microdissected sample. After the extraction fluid has had sufficient time to react with the microdissected sample, the bi-position pump blister 1595 can be further actuated to force extraction fluid that is carrying aspects of the sample toward the exit port 1520.

Example 3

Referring now to FIGS. 16-22, another single stage extraction device and a method for manufacture thereof will now be described. The device will be described first, then the component parts of the device will be described, then the process of making the device will be described, and then the process of operating the device will be described.

Referring to FIG. 21E, the assembled single stage extraction device is depicted. This device includes a spacer 2170 that defines in-part an extraction chamber 2180. More generically, the extraction chamber 2180 can be termed a reaction chamber. The extraction chamber 2180 is coupled to first capillary 2130. The first capillary 2130 is coupled to a fill port 2110. The extraction chamber 2180 is also coupled to a second capillary 2140. It can be appreciated that the spacer 2170 overlies and is aligned with the two capillary stop junction holes 2160. Thus, the interior of the spacer 2170 defines the extraction chamber 2180. The spacer 2170 includes a mating surface 2190. The mating surface 2190 is for attachment (mating) to a biological sample carrier (not shown in FIG. 21E), for example, a laser capture microdissection transfer film carrier.

Referring to FIGS. 21A-21E, the component parts of the single stage extraction device are depicted. Referring to FIG. 21A, the bottom laminate reflects the outline of the device and includes no specific additional structural features. Referring to FIG. 21B, the middle laminate layer 2120 includes a fill port 2110. The fill port 2110 is connected to a first capillary 2130. The middle laminate 2120 also includes a second exit capillary 2140. The fill port 2110, the first capillary 2130, and the second capillary 2140 can all be seen in FIG. 18.

Referring to FIG. 21C, the top laminate 2150 of the single stage extraction device is depicted. The top laminate 2150 includes a fill port hole 2155 and two capillary stop junction holes 2160. The capillary stop junction holes 2160 in the top laminate 2150 align with the ends of the capillaries 2130 and 2140 depicted in FIG. 21B. Similarly, the fill port hole 2155 in FIG. 21C aligns with the fill port 2110 in FIG. 21B.

Referring to FIG. 21D, a spacer 2170 in the form of a ring is depicted. The spacer 2170 includes a microdissected sample film carrier mating surface 2175.

Figure 16:
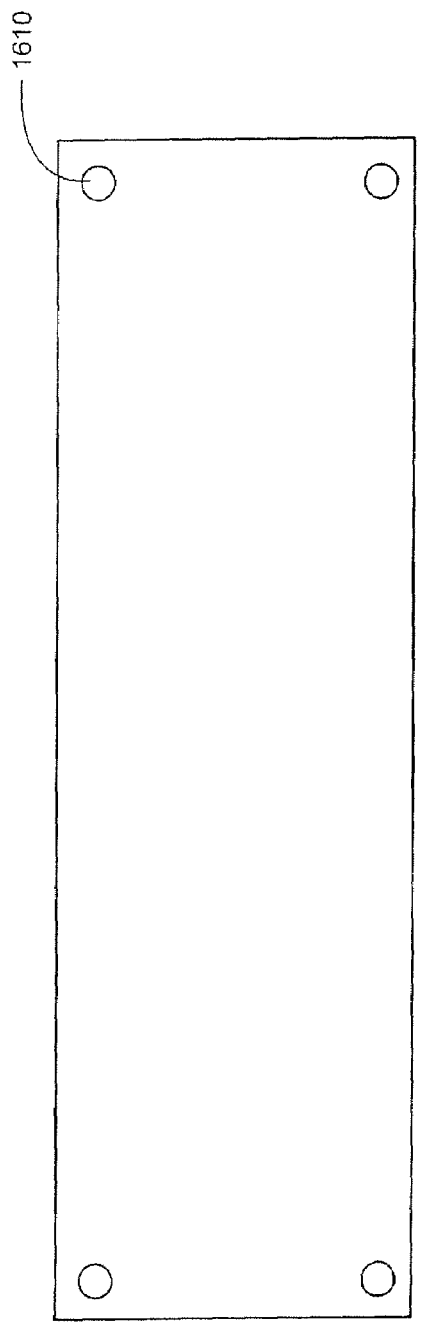
FIG. 16 illustrates a top schematic view of a bottom laminate, representing an embodiment of the invention.

Referring to FIGS. 16-20, a series of laminate stock strips are depicted. Referring to FIG. 16, a laminate stock strip for the bottom laminate is shown. The bottom laminate includes four tooling pin holes 1610. The bottom laminate should be a hydrophilic polymer, for example, a polyester with an optional surfactant treatment. For example a suitable hydrophilic polymer are those manufactured to have anti-fog properties.

Figure 17:
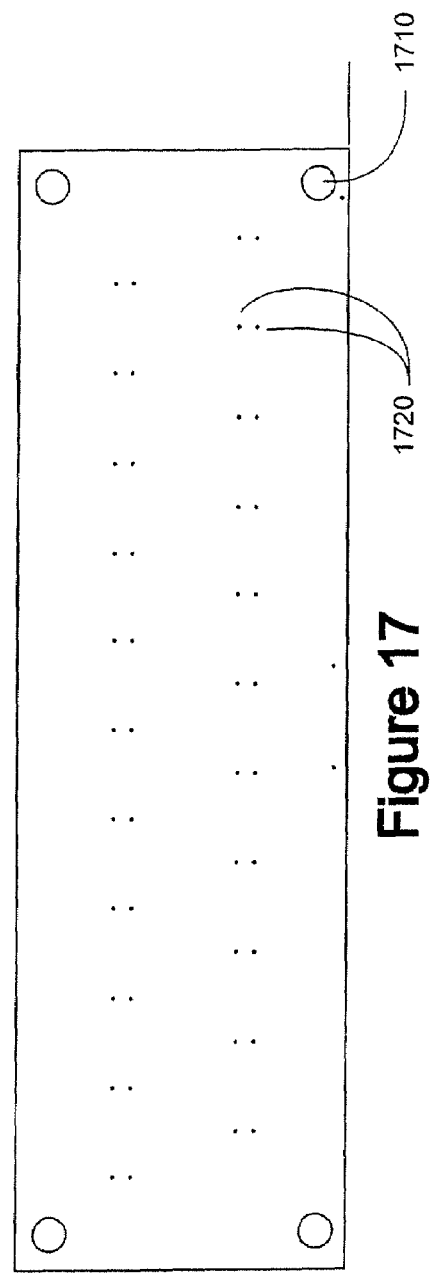
FIG. 17 illustrates a top schematic view of a top laminate, representing an embodiment of the invention.

Referring to FIG. 17, a laminate stock strip for the top laminate is depicted. The laminate stock strip for the top laminate includes four tooling pin holes 1710 and a number of stop junction holes 1720. Each laminate stock strip includes two rows of single stage extraction devices (depicted in FIG. 21). Each of the single stage extraction devices has a top laminate portion with two stop junction holes 1720. A variety of exemplary dimensions in inches are shown in FIG. 17. Of course, the invention is not limited to any of the specific dimensions. The top laminate stock strip material should be a hydrophilic polymer, again for example, a polyester with optional surfactant treatment. Again it useful if the hydrophilic polymer has anti-fog properties.

Figure 18:
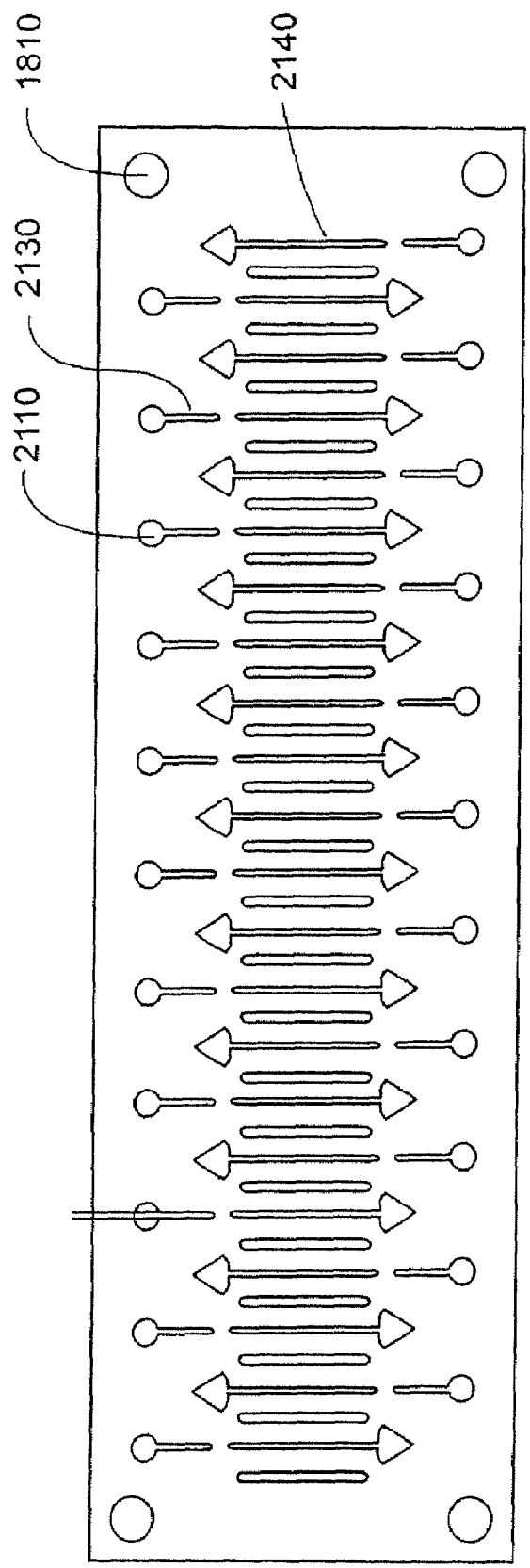
FIG. 18 illustrates a top schematic view of a middle laminate before cutting, representing an embodiment of the invention.

Referring to FIG. 18, a laminate stock strip for the middle laminate is depicted. The middle laminate includes four tooling pin holes 1810 and a number of other structural features. The middle laminate often is chosen to have pressure sensitive adhesive on both surfaces. A variety of exemplary dimensions in inches are shown in FIG. 18. Of course, the invention is not limited to any specific dimensions. It can be appreciated from FIG. 18 that the two rows of single stage extraction devices point toward one another on this stock strip. The top, middle, and bottom films are assembled using the alignment holes 1610,1710, and 1810 to align the three layers. The assembly can be pressed together using a hand roller, or a rolling mill or other techniques known to those skilled in the art.

Figure 19:
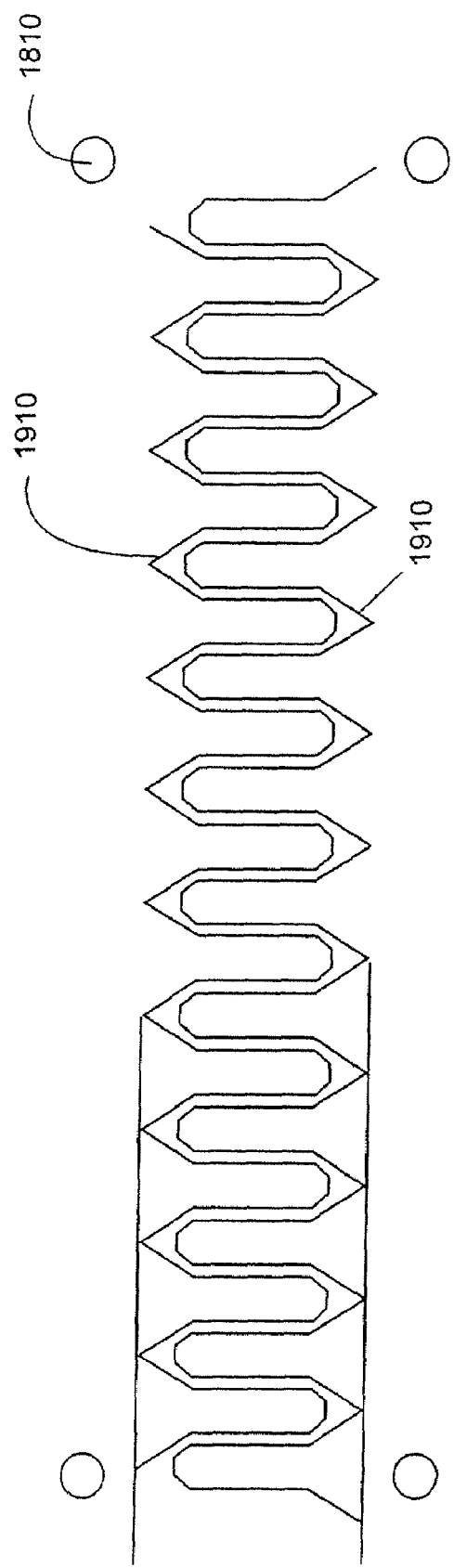
FIG. 19 illustrates a schematic view of a laser cutting pattern for the middle laminate depicted in FIG. 18, representing an embodiment of the invention.

Referring to FIG. 19, a laser cutting track for the perforated laminate assembly is depicted. This cutting track separates the double row of devices illustrated in FIGS. 16, 17 and 18 into two separate single rows. The devices or darts can then be individually separated using a simple cutting device such as a scissors. Again, a variety of exemplary dimensions are depicted in FIG. 19 and the invention is not limited to these dimensions. In more detail, the perforated laminate stock strip depicted in FIG. 18 is located with respect to the pin holes 1810 and processed by a carbon dioxide laser to form the cut lines 1910 that are depicted in FIG. 19.

Figure 20:
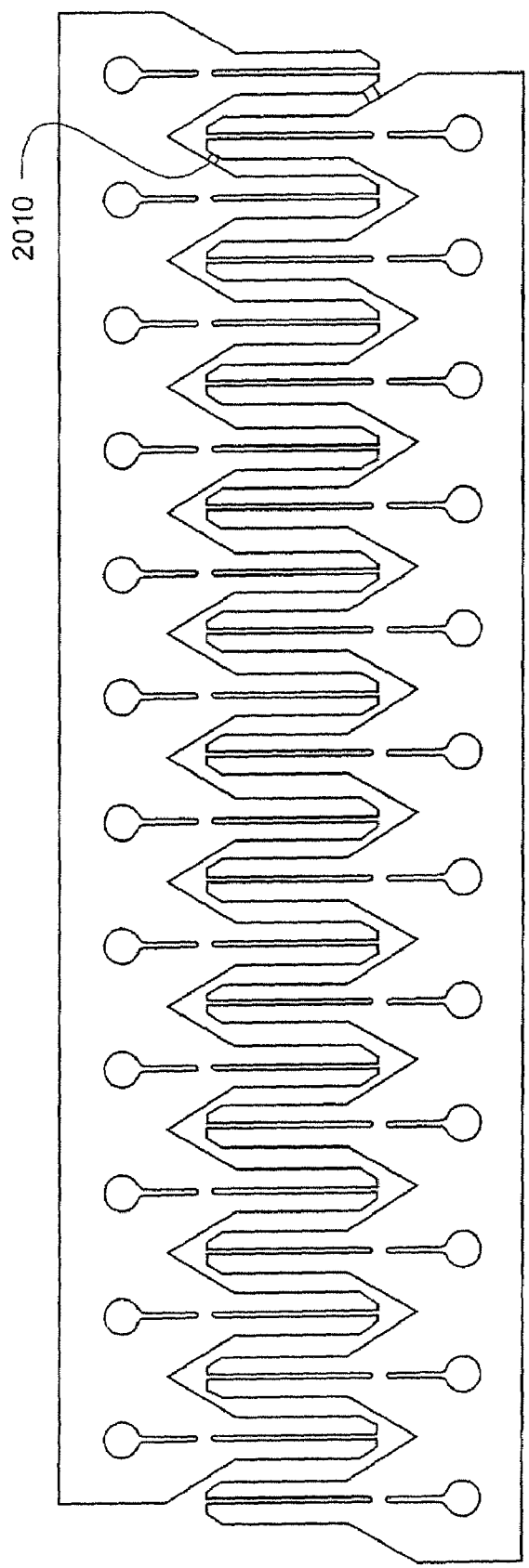
FIG. 20 illustrates a top schematic view of a middle laminate after cutting, representing an embodiment of the invention.
Figure 21:
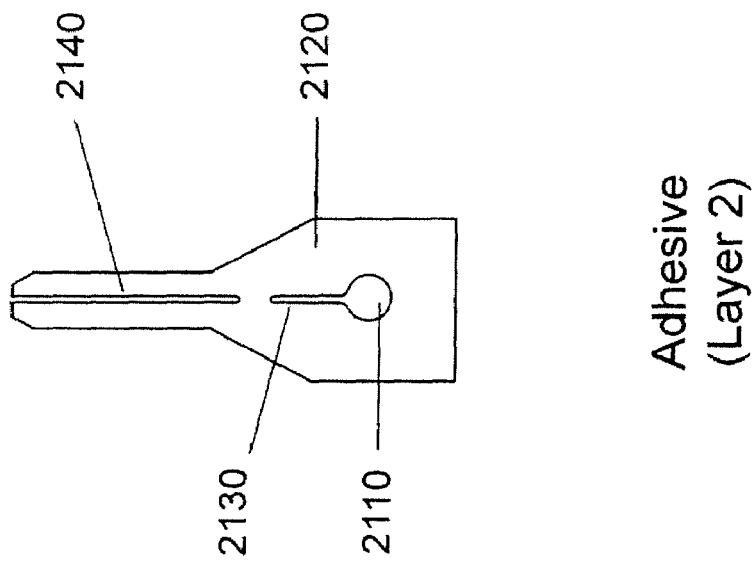
FIG. 21A illustrates a top schematic view of the bottom laminate of a single stage microdissected sample extraction device, representing an embodiment of the invention.
FIG. 21B illustrates a top schematic view of the middle laminate of a single stage microdissected sample extraction device, representing an embodiment of the invention.
FIG. 21C illustrates a top schematic view of the top laminate of a single stage microdissected sample extraction device, representing an embodiment of the invention.
FIG. 21D illustrates a top schematic view of the spacer of a single stage microdissected sample extraction device, representing an embodiment of the invention.
FIG. 21E illustrates a top schematic view of the assembled single stage microdissected sample extraction device, representing an embodiment of the invention.
Figure 21:
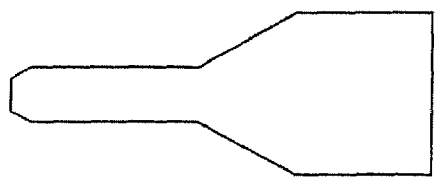
Figure 21:
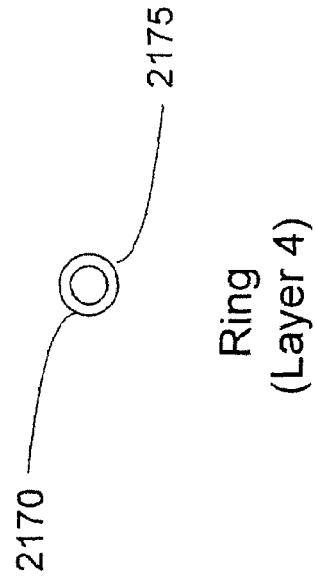
Figure 21:
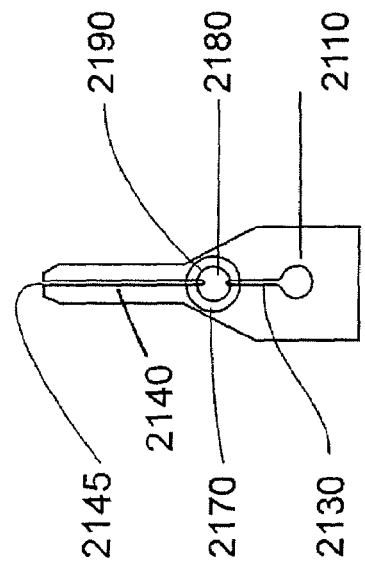
Figure 21:
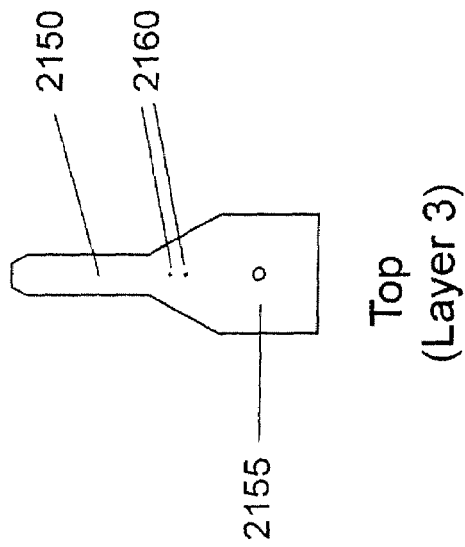

Referring to FIG. 20, the laser cut laminate stock strip that results from processing the strip shown in FIG. 18 in accordance with the trace shown in FIG. 19 is shown. The two parallel, facing rows of single stage extraction devices can be held together with tabs 2010 provided that the cutting trace is appropriately interrupted.

The operation of this single stage extraction device will now be described. A transfer film (not shown) carrying a microdissected sample can be mated with the microdissected sample film carrier mating surface 2175, thereby completing the extraction chamber 2180. An extraction fluid is applied to the fill port 2110 with sufficient volume to fill the extraction chamber and fill capillary 2130. Capillary forces draw the extraction fluid into the fill capillary 2130 and extraction chamber formed by ring 2170 and the transfer film. Stop junction forces prevent the fluid from exiting the extraction chamber. Alternatively, by placing the composite system into a microcentrifuge tube and spinning, the extraction fluid in the fill port 2110 will be driven through the first capillary 2130 to the extraction chamber 2180 whereupon it will react with (aka digest) the microdissected sample. By increasing the rpm of the centrifuge, the extraction fluid that carries portions (or all) of the microdissected sample will pass from the extraction chamber 2180 into the second capillary 2140 and thence pass out of the single stage extraction device at a tip 2145. The size of the first or entrance stop junction hole 1720 can be made slightly larger than the exit stop junction hole in order to provide greater stop junction forces at this junction, holding the extraction fluid in the extraction chamber until the centrifuge rpm is increased. Since the entire assembly has been previously placed in the microcentrifuge tube, fluid carrying digested sample which passes out of the tip 2145 will be caught and captured in the microcentrifuge tube. Extraction devices of this type can be termed "darts" because of their overall appearance.

Figure 22:
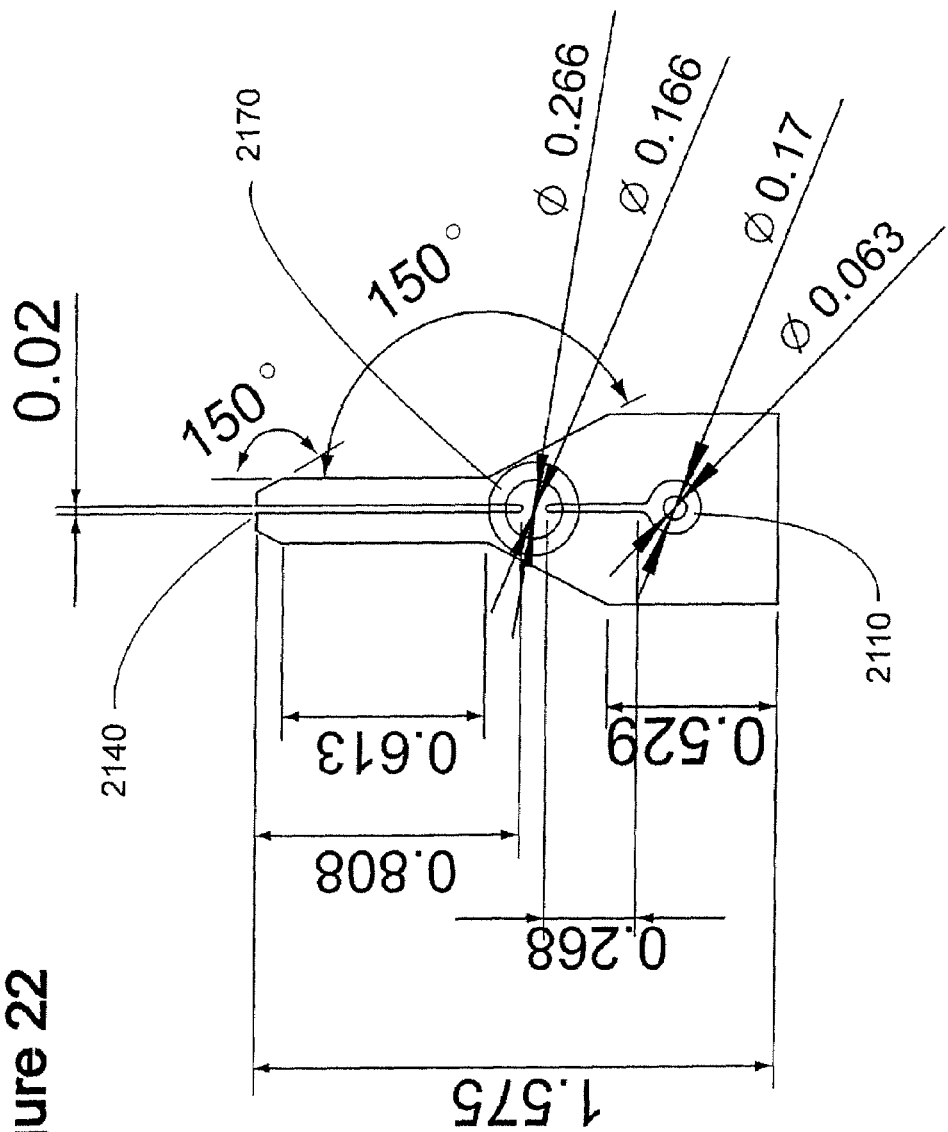
FIG. 22 illustrates a top detail view of the microdissected sample extraction device depicted in FIG. 21E, representing an embodiment of the invention.

Referring to FIG. 22, a number of exemplary dimensions relating to this single stage extraction device are shown. Of course, the invention is not limited to any specific dimensions.

It can be appreciated that reaction buffer from fill port 2110 will be contained by spacer 2170 and eventually pass through the second capillary 2140.

Example 4

Figure 23:
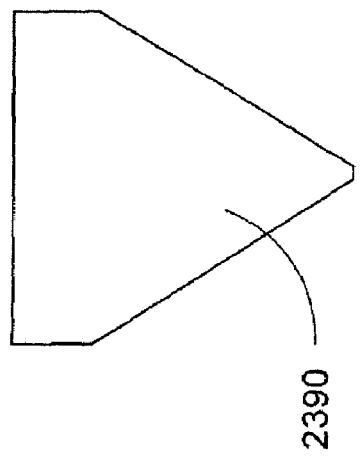
FIG. 23A illustrates a top schematic view of the bottom laminate of a two stage microdissected sample extraction device, representing an embodiment of the invention.
FIG. 23B illustrates a top schematic view of the middle laminate of a two stage microdissected sample extraction device, representing an embodiment of the invention.
FIG. 23C illustrates a top schematic view of the top laminate of a two stage microdissected sample extraction device together with a foam ring and coversheet with hole for pumping sample and dilutent, representing an embodiment of the invention.
FIG. 23D illustrates a top schematic view of the extraction chamber defining spacer of the two stage microdissected sample extraction device together with a release layer, representing an embodiment of the invention.
FIG. 23E illustrates a top schematic view of a dilution chamber defining spacer of the two stage microdissected sample extraction device, representing an embodiment of the invention.
FIG. 23F illustrates a top schematic view of a cover for the extraction chamber defining spacer of the two stage microdissected sample extraction device, representing an embodiment of the invention.
FIG. 23G illustrates a top detail view of the assembled two stage microdissected sample extraction device, representing an embodiment of the invention.
Figure 23:
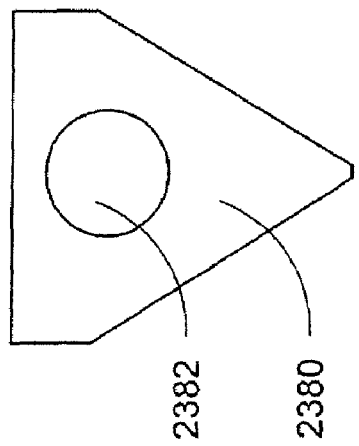
Figure 23:
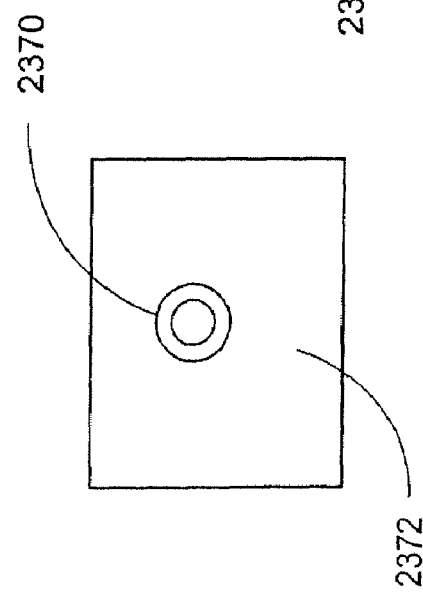
Figure 23:
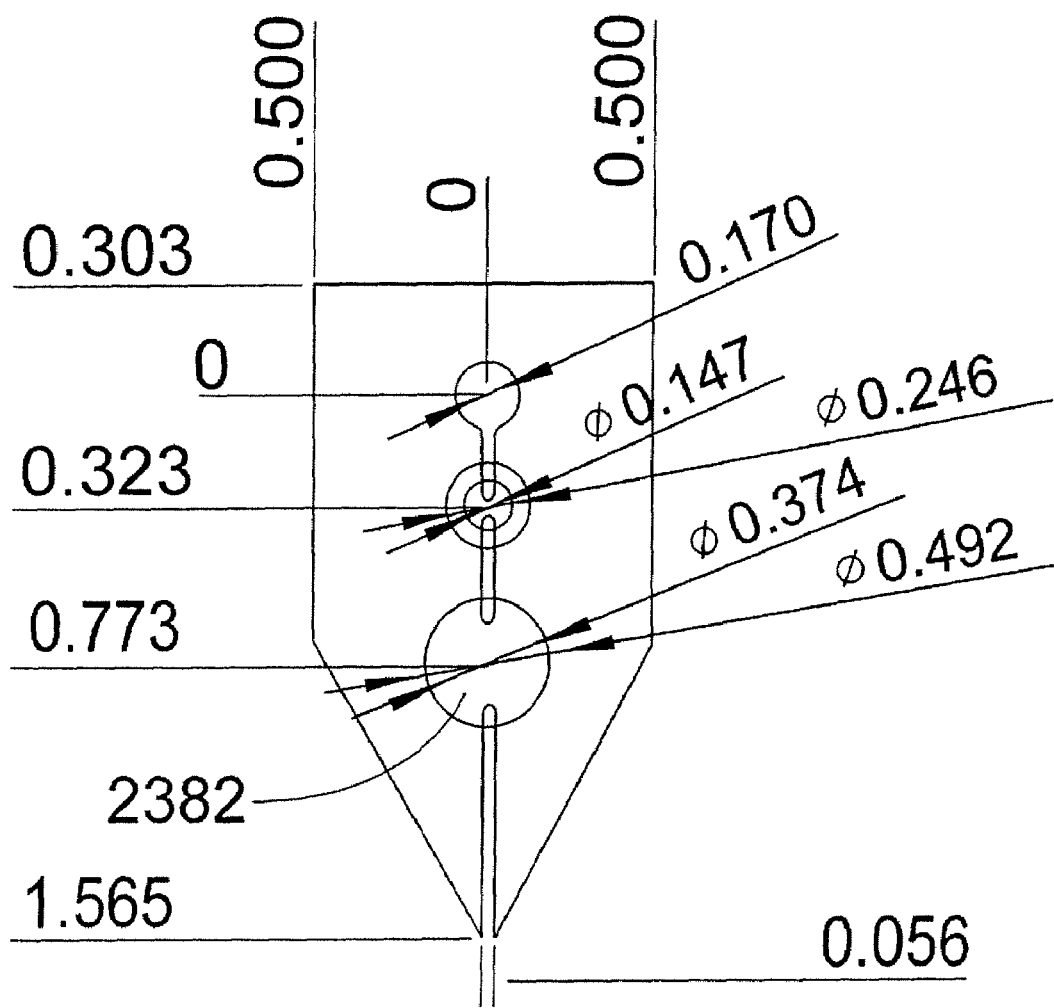

Referring to FIGS. 23A-23G, a two stage extraction device is depicted. Referring to FIG. 23A, in this embodiment, the bottom laminate 2310 includes four capillary stop junction holes 2320. These stop junction holes can be of slightly different diameters thus requiring different pressures for the fluid to pass through the stop junction.

Referring to FIG. 23B, the middle laminate 2330 includes a fill port 2335. A first capillary 2340 is coupled to the fill port 2335. The middle laminate 2330 includes a second capillary 2345. The middle layer 2330 also includes a third capillary 2350 which terminates at a tip 2355.

Referring to FIG. 23C, a top laminate 2360 includes a layer of foam 2362 defining a pump space 2364. The top laminate 2360 includes a hole 2366. A cover sheet 2368 is placed over the layer of foam 2362.

Referring to FIG. 23D, a spacer 2370 in the form of a ring is shown coupled to a release layer 2372. The ring can be a piece of plastic with adhesive on both sides. The release layer 2372 can be a piece of silicone coated paper.

Referring to FIG. 23E, a layer of foam 2380 with pressure sensitive adhesive on both sides has a hole 2382. The hole 2382 will define a dilution chamber. Referring to FIG. 23F, a cover layer 2390 is depicted. The cover layer 2390 is placed on top of foam 2380.

Referring now to FIG. 23G, the assembled two stage extraction device is depicted. FIG. 23G shows a number of exemplary dimensions associated with the two stage extraction device. Of course, the invention is not limited to any particular dimensions.

The operation(s) of this two stage extraction device will now be described. A reaction buffer (aka extraction fluid) can be located in the fill port 2335 before shipment from the manufacturer or can be placed in the well by the end user. When ready for use, the release layer 2372 is removed from the spacer 2370 and a sample film carrier (not shown) is mated with the microdissected sample film carrier mating surface of the spacer 2370 such that the microdissected sample is introduced into the extraction chamber. The extraction buffer is then applied to the fill port 2335. The hole in the cover sheet 2368 is then covered and the pump is actuated by compressing the foam 2362 to initiate pumping, thereby forcing reaction buffer in the fill port 2335 through the capillary 2340 and then into the extraction chamber. After extraction is complete, dilutent is applied to the entrance port 2335. The pump is be actuated by compression (i.e., depressing the cover 2362). Reaction buffer, microdissected sample, and the dilutent will then be forced from the extraction chamber into the dilution chamber defined by hole 2382. In this way, the microdissected sample can be processed by a first volume of reaction buffer that is then increased to a second volume by the addition of the dilution fluid. This has significant advantages in that the very small microdissected sample can be processed by a correspondingly small amount of reaction buffer while subsequent processing can be carried out on a larger volume of material that includes the dilution fluid. By continuing to actuate the second pump, the dilution product can be forced through the third capillary 2350 toward the tip 2355. Other reagents could be coated within the capillaries and/or stop junction holes.

Practical Applications of the Invention

A practical application of the invention that has value within the technological arts is the extraction of organic molecules from microdissected samples. Further, the invention is useful in conjunction with analyzing DNA (useful for the purpose of determining susceptibility to disease), or in conjunction with identifying malignancies (useful for the purpose of diagnosis), or the like. There are virtually innumerable uses for the invention, all of which need not be detailed here.

ADVANTAGES OF THE INVENTION

An extraction device, representing an embodiment of the invention, can be cost effective and advantageous for at least the following reasons. The invention permits small microdissected samples to be digested by small volumes of reagents. The invention permits small digested volumes to be diluted to larger volumes. The invention permits processing of microdissected sample in an economic manner.

All the disclosed embodiments of the invention described herein can be realized and practiced without undue experimentation. Although the best mode of carrying out the invention contemplated by the inventors is disclosed above, practice of the invention is not limited thereto. Accordingly, it will be appreciated by those skilled in the art that the invention may be practiced otherwise than as specifically described herein.

For example, the individual components need not be formed in the disclosed shapes, or assembled in the disclosed configuration, but could be provided in virtually any shape, and assembled in virtually any configuration. Further, the individual components need not be fabricated from the disclosed materials, but could be fabricated from virtually any suitable materials. Further, although the extraction devices described herein can be physically separate modules, it will be manifest that the extraction devices may be integrated into the apparatus with which they are associated. Furthermore, all the disclosed elements and features of each disclosed embodiment can be combined with, or substituted for, the disclosed elements and features of every other disclosed embodiment except where such elements or features are mutually exclusive.

It will be manifest that various additions, modifications and rearrangements of the features of the invention may be made without deviating from the spirit and scope of the underlying inventive concept. It is intended that the scope of the invention as defined by the appended claims and their equivalents cover all such additions, modifications, and rearrangements. The appended claims are not to be interpreted as including means-plus-function limitations, unless such a limitation is explicitly recited in a given claim using the phrase "means-for." Expedient embodiments of the invention are differentiated by the appended subclaims.

What is claimed is:

1. A biological sample processing system, comprising:
    a sample processing device;
    a biological sample carrier having a surface; and
    a transfer film on the surface of the carrier;
    wherein the carrier is adapted to mate with the device to form a chamber defined in part by the carrier such that at least a portion of the transfer film is included in the chamber; the carrier being adapted to position a biological sample within the chamber upon mating the carrier to the device;
wherein the sample processing device further includes a dilution chamber.

2. The biological sample processing system of claim 1, wherein the chamber is an extraction chamber.

3. A biological sample processing system, comprising:
a sample processing device; and
a biological sample carrier having a surface adapted to have a biological sample attached to the surface;
wherein the carrier is adapted to mate with the device to form a reaction chamber defined in part by the carrier such that at least a portion of the surface adapted to have a biological sample attached is included in the chamber; the carrier being adapted to introduce the sample to the reaction chamber upon mating the carrier to the device;
wherein the sample processing device further includes a dilution chamber.

4. A biological sample processing system, comprising:
a sample processing device; and
a biological sample carrier having a surface adapted to have a biological sample attached to the surface;
wherein the carrier is adapted to mate with the device to form a reaction chamber defined in part by the carrier such that at least a portion of the surface adapted to have a biological sample attached is included in the chamber; the carrier being adapted to introduce the sample to the reaction chamber upon mating the carrier to the device;
wherein the sample processing device includes a pump.

5. The biological sample processing system of claim 1, wherein the sample processing device comprises a centrifuge tube.

6. A biological sample processing system, comprising:
a sample processing device; and
a biological sample carrier having a surface adapted to have a biological sample attached to the surface;
wherein the carrier is adapted to mate with the device to form a reaction chamber defined in part by the carrier such that at least a portion of the surface adapted to have a biological sample attached is included in the chamber; the carrier being adapted to introduce the sample to the reaction chamber upon mating the carrier to the device;
wherein the sample processing device is a laminated assembly.

7. A biological sample processing system, comprising:
a sample processing device; and
a biological sample carrier having a surface adapted to have a biological sample attached to the surface;
wherein the carrier is adapted to mate with the device to form a reaction chamber defined in part by the carrier such that at least a portion of the surface adapted to have a biological sample attached is included in the chamber; the carrier being adapted to introduce the sample to the reaction chamber upon mating the carrier to the device;
wherein the sample processing device is a laminated assembly and centrifuge tube.

8. A biological sample processing system, comprising:
a sample processing device including:
a first chamber having an opening, a first port, and a second port; and
a second chamber fluidly coupled to the first chamber via the second port; and
a sample carrier having a surface adapted to have a biological sample attached to the surface; the sample carrier being adapted to mate with the device to close the opening on the first chamber such that at least a portion of the surface adapted to have the biological sample attached is included in the first chamber; the carrier being adapted to position the sample within the first chamber upon mating the carrier to the device.

9. A biological sample processing system, comprising:
a sample processing device including:
a first chamber having a first port and a second port; and
a second chamber fluidly coupled to the first chamber via the second port; and
a sample carrier having a surface adapted to have a biological sample attached to the surface; the sample carrier being adapted to mate with the device to form the first chamber defined in part by the sample carrier such that at least a portion of the surface adapted to have a biological sample attached is included in the first chamber; the carrier being adapted to introduce the sample to the reaction chamber upon mating the carrier to the device;
wherein the second port is a stop junction.

10. A biological sample processing system, comprising:
a sample processing device including:
a first chamber having an opening, a first port, and a second port; and
a second chamber fluidly coupled to the first chamber via the second port;
wherein the sample processing device includes a centrifuge tube; and
a sample carrier having a surface adapted to have a biological sample attached to the surface; the sample carrier being adapted to mate with the device to close the opening on the first chamber such that at least a portion of the surface adapted to have the biological sample attached is included in the first chamber; the carrier being adapted to position the sample within the first chamber upon mating the carrier to the device.

11. A biological sample processing system, comprising:
a sample processing device including:
a first chamber having a first port, a second port and a third port;
a first conduit;
a second chamber fluidly coupled to the first chamber via the second port and the first conduit; and
a second conduit fluidly coupled to the first chamber via the third port; and
a sample carrier having a surface adapted to have a biological sample attached to the surface; the sample carrier being adapted to mate with the device to form the first chamber defined in part by the sample carrier such that at least a portion of the surface adapted to have a biological sample attached is included in the first chamber; the carrier being adapted to introduce the sample to the first chamber upon mating the carrier to the device.

12. The biological sample processing system of claim 11, wherein the second chamber is a fluid reservoir.

13. The biological sample processing system of claim 11, wherein the second chamber includes a pump.

14. The biological sample processing system of claim 11, wherein the sample processing device further includes a third chamber fluidly coupled to the first chamber via the second conduit.

15. The biological sample processing system of claim 14, wherein the sample processing device further includes a third conduit fluidly coupled to the third chamber.

16. The biological sample processing system of claim 11, wherein the sample processing device is a laminated assembly.

17. The biological sample processing system of claim 16, wherein the laminated assembly includes:

a first layer;

a second layer defining the second chamber, first conduit and second conduit;

a third layer defining a fill port and stop junction holes; and a fourth layer defining the first chamber;

wherein the second layer is located between the first layer and third layer; the third layer being located between the second layer and fourth layer.

18. The biological sample processing system of claim 1, wherein the chamber is a reaction chamber.

19. The biological processing system of claim 8, wherein the first chamber is an extraction chamber.

20. The biological processing system of claim 8, wherein the first chamber is a reaction chamber.

21. The biological processing system of claim 10, wherein the first chamber is an extraction chamber.

22. The biological processing system of claim 10, wherein the first chamber is a reaction chamber.

23. A sample processing system, comprising:

a sample processing device; and a biological sample carrier having a surface adapted to have a microdissected sample attached to the surface;

wherein the carrier is adapted to mate with the device to form a chamber defined in part by the carrier such that at least a portion of the surface adapted to have a microdissected sample attached is included in the chamber; the carrier being adapted to position the sample within the chamber upon mating the carrier to the device;

wherein the sample processing device further includes a dilution chamber.

24. The biological processing system of claim 23, wherein the first chamber is an extraction chamber.

25. The biological processing system of claim 23, wherein the first chamber is a reaction chamber.

26. The biological processing system of claim 1, wherein the sample processing device includes a pump.

27. The biological processing system of claim 1, wherein the sample processing device is a laminated assembly.

28. The biological processing system of claim 1, wherein the sample processing device comprises a centrifuge tube.

29. The biological processing system of claim 8, wherein the second port is a stop junction.

30. The biological processing system of claim 1, wherein the sample processing device comprises a fluidic circuit.

31. The biological processing system of claim 8, wherein the sample processing device comprises a fluidic circuit.

32. The biological processing system of claim 23, wherein the sample processing device comprises a fluidic circuit.

33. The biological processing system of claim 23 wherein the surface is a transfer film attached to the carrier.

* * * * *